United States Patent [19]
Filipi et al.

[11] Patent Number: 5,088,979
[45] Date of Patent: Feb. 18, 1992

[54] METHOD FOR ESOPHAGEAL INVAGINATION AND DEVICES USEFUL THEREIN

[75] Inventors: Charles J. Filipi, Marshalltown, Iowa; Tom R. DeMeester, San Marino, Calif.; Rebecca C. Gibbs, Burlington, N.C.; Ronald A. Hinder, Omaha, Nebr.

[73] Assignee: Wilson-Cook Medical Inc., Winston-Salem, N.C.

[21] Appl. No.: 608,339

[22] Filed: Nov. 2, 1990

Related U.S. Application Data

[63] Continuation-in-part of Ser. No. 595,977, Oct. 11, 1990.

[51] Int. Cl.⁵ .............................................. A61M 37/00
[52] U.S. Cl. ....................................... 604/26; 604/174
[58] Field of Search ...................... 604/26, 174; 128/4

[56] References Cited

U.S. PATENT DOCUMENTS

| | | | |
|---|---|---|---|
| 3,817,251 | 6/1974 | Hasson | 604/26 |
| 4,077,412 | 3/1978 | Moosun | 604/174 X |
| 4,207,872 | 6/1980 | Meiri et al. | 128/4 |
| 4,240,411 | 12/1988 | Hosono | 128/4 |
| 5,002,557 | 3/1991 | Hasson | 604/26 X |

Primary Examiner—William H. Grieb
Attorney, Agent, or Firm—Woodard, Emhardt, Naughton, Moriarty & McNett

[57] ABSTRACT

A technique for invaginating the esophagus at the gastroesophageal junction is disclosed, as well as an invagination device useful in the described technique. The invagination device includes an introducer guide which has an outside diameter approximating that of the esophagus and a plurality of needle-receiving lumens extending to its outer diametric surface. The invagination device also has an engagement assembly which includes 10 needles, each having a retracted position in which they lie within the needle-receiving lumens of the introducer guide, and an extended position in which they extend out of the lumens and project radially from the guide for engagement with the esophagus at the gastroesophageal junction. The invagination device is introduced transorally into the esophagus, its engagement assembly is activated to place the needles in their extended position in engagement with the esophagus, and the engaged invagination device is advanced the toward the stomach to fold the attached esophagus beyond the gastroesophageal junction. A remotely operable fastening assembly, which has been introduced into the stomach through an operating channel/insufflation port, is then operated to fasten the invaginated gastroesophageal junction to the surrounding involuted fundic wall. Finally, the needles are retracted back into their needle-receiving lumens and the invagination device and the fastening assembly are removed from the body of the patient. This minimally-invasive technique accomplishes the formation of a new valve between the esophagus and stomach, thus preventing acid reflux.

39 Claims, 8 Drawing Sheets

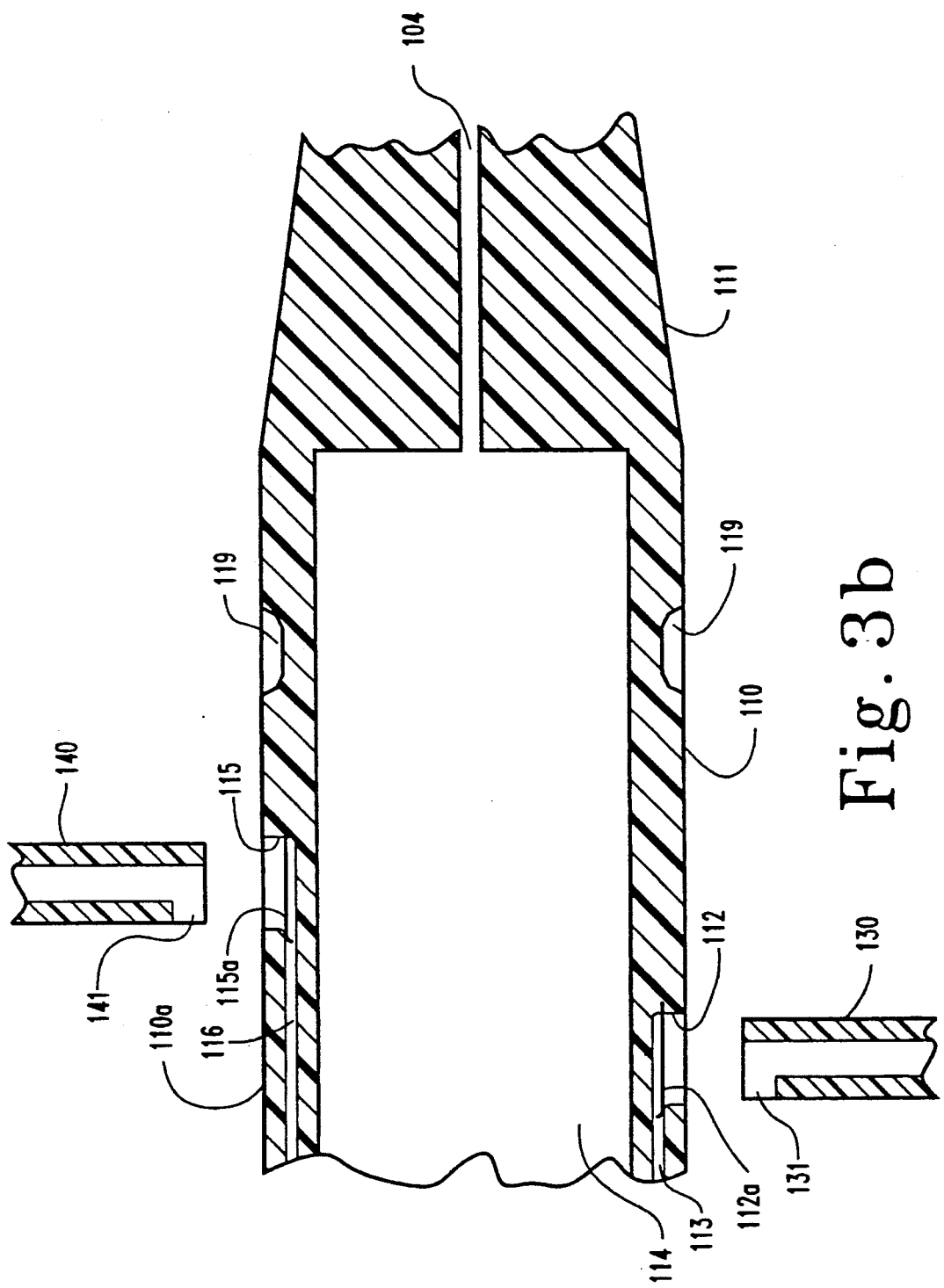

METHOD FOR ESOPHAGEAL INVAGINATION AND DEVICES USEFUL THEREIN

REFERENCE TO RELATED APPLICATIONS

This application is a continuation-in-part of pending U.S. patent application Ser. No. 07/595,977, filed on Oct. 11, 1990 and entitled Method and Device for Esophageal Invagination.

BACKGROUND OF THE INVENTION

The present invention relates to the treatment of gastroesophageal reflux disease. More specifically, the present invention relates to a new and unique method for minimally-invasive invagination of the esophagus at the gastroesophageal junction and to devices which are useful in this newly developed procedure.

Patients with gastroesophageal reflux disease are prone to esophagitis, ulceration, stricture formation and columnar metaplasia of the normal squamous lining. The latter, termed Barretts esophagus, occurs in about 10% of patients with gastroesophageal reflux disease and is associated with the presence of stricture, deep ulcers and the development of adenocarcinoma. Gastroesophageal reflux disorders are diagnosed in over 500,000 people in the U.S. each year with only approximately 35,000 undergoing corrective anti-reflux.

There is a need for a new approach to the treatment of gastroesophageal reflux disease that would be less invasive than general surgical techniques and more cost-effective than chronic acid reduction therapy. The availability of such a procedure would lead to earlier and more widespread referral for corrective surgery and thus the avoidance of severe complications caused by progression of the disease while undergoing long term medical therapy.

SUMMARY OF THE INVENTION

Generally speaking, the present invention provides a new and improved method for treating gastroesophageal reflux by the endoscopic construction of a fundoplication, and to new devices which are useful in this new technique. According to one embodiment of the method, an invagination device is introduced transorally into the esophagus. The invagination device includes an introducer guide which has an outside diameter approximating that of the esophagus and a plurality of needle-receiving lumens extending to its outer diametric surface. The invagination device also has an engagement assembly which includes a number of needles. These needles each have a retracted position in which they lie within the needle-receiving lumens and project radially from the guide for engagement with the esophagus. The engagement assembly is then activated to place the needles in their extended position in engagement with the esophagus, and the engaged invagination device is advanced toward and into the stomach to invaginate the gastroesophageal junction into the stomach for a distance of 3-4 cm. A remotely operable fastening assembly is introduced into the stomach through a previously implanted operating channel/insufflation port, and operated to fasten the invaginated esophagus to the adjacent involuted stomach. This is performed by sliding one arm of the fastening assembly into preformed grooves in the surface of the invagination device and placing the other arm over the involuted stomach, then stapling the invaginated esophageal wall to the involuted gastric wall in a non-crushing manner. After this "nipple" valve has been secured by the fastening assembly, the needles are retracted back into their needle-receiving lumens, and the invaginated device and the fastening assembly are removed. The implanted operating channel/insufflation ports are sealed and left in place for a period of time after removal of the other instrumentation in order to maintain fixation of the newly formed valve.

This new minimally-invasive approach accomplishes the formation of a new valve between the esophagus and stomach, thus preventing acid refluxation.

BRIEF DESCRIPTION OF THE DRAWINGS

FIG. 1a shows an invagination device that has been advanced into the esophagus and positioned at the gastroesophageal junction. FIG. 1b shows the invagination device of FIG. 1a with its engagement assembly having been activated to extend a plurality of needles into engagement with the esophagus near the esophageal junction (engagement of needles should be made as close to the gastroesophageal junction as practicable). FIG. 1c shows the engaged invagination device having been advanced toward the stomach to invaginate the esophageal wall at the gastroesophageal junction, and further illustrate the invaginated gastroesophageal junction being fastened into place. Lastly, FIG. 1d shows the newly formed valve between the esophagus and the stomach, with the invagination device and other equipment having been removed.

FIG. 2a shows the device with its engagement assembly deactivated, the engagement needles being retained within their respective lumens. FIG. 2b shows the device with its engagement assembly activated to project the needles from their respective lumens for engagement with the esophageal wall.

FIGS. 3a–d illustrate an operating channel/insufflation assembly which provides percutaneous access into the stomach for introduction of a remotely operable fastener and/or endoscope, and also provides for the insufflation of the stomach. FIGS. 3a is a side elevational view of a complete assembly. FIGS. 3b–d illustrate enlarged cross-sectionals view of portions of the assembly at various stages of operation. FIG. 3b shows an implanted operating channel/insufflation port 110, balloon inflation nozzle 130, and insufflation valve 140, with nozzle 130 and valve 140 detached from their respective connection ports. In FIG. 3c, tapered portion 111 of port 110 has been severed, and fastening assembly 50 has been inserted through central operating channel 114. Also in FIG. 3c, insufflation valve 140 has been attached to insufflation port 115 for insufflation of the stomach through insufflation lumen 116, and sealing member 150 has been placed about port 110 and positioned in sealing engagement with fastening assembly 50, thus preventing gas leakage through operating channel 114 during the operation/insufflation. In FIG. 3d, fastening assembly 50 has been removed, insufflation valve 140 has been detached, and seal cap 160 has been placed about port 110, sealing access to and from the stomach.

In the same manner as FIGS. 1a–d, FIGS. 4a–d illustrate sequential stages in the performance of an invagination technique according to the present invention in conjunction with an alternatively configured invagination device.

FIG. 5a shows an enlarged end view of invagination guide 70', illustrating the circumferential spacing of lumens 78' and grooves 72'. FIG. 5b is an enlarged fragmented side elevational view of invagination guide 70' showing groove 72' extending past lumens 78'.

DESCRIPTION OF THE PREFERRED EMBODIMENT

Figures 1A, 1B:
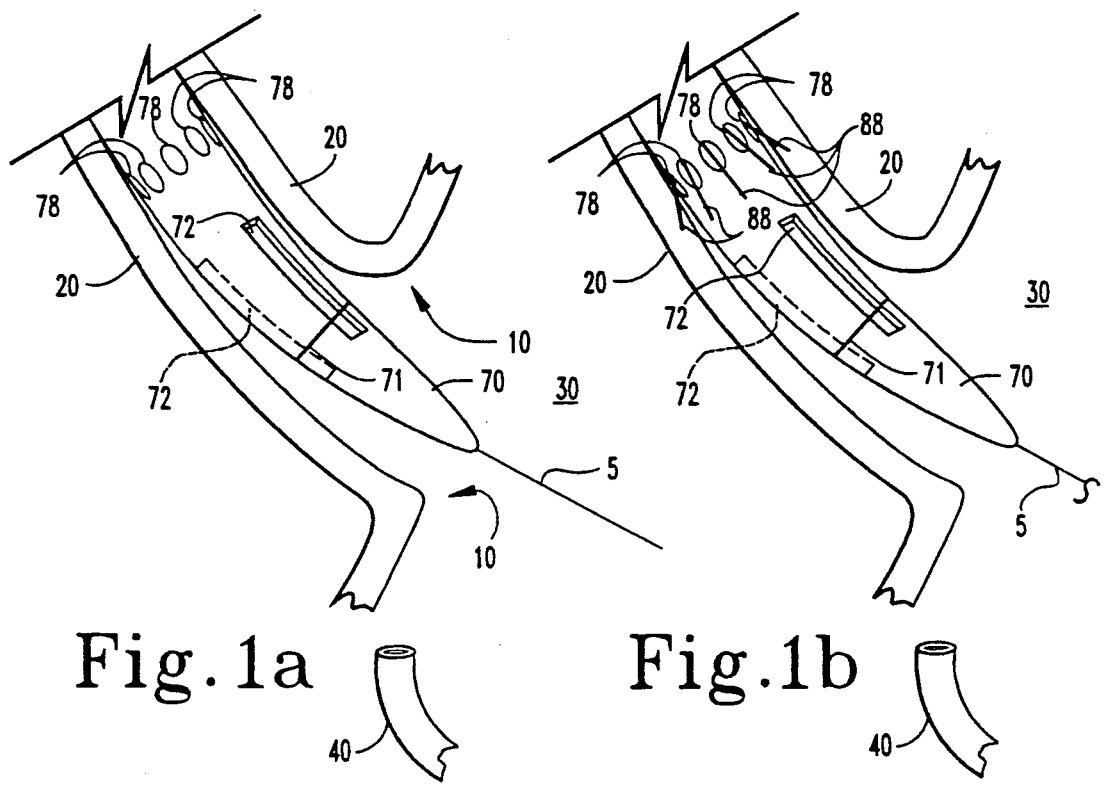
FIGS. 1a–d conceptually illustrate sequential stages in the performance of an invagination technique according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The preferred embodiment of the method of the present invention will now be described with reference to FIGS. 1a–d which illustrate sequential stages in the performance of this invagination technique at the gastroesophageal junction 10 which anatomically connects the esophagus 20 to the stomach 30.

Preliminarily, two operating channel/insufflation ports are percutaneously opened into the stomach 30, one port being sized to accommodate an endoscope (7 mm), and the second port being about 12 mm in diameter to accommodate a remotely operable fastening assembly. This is generally accomplished by 1) percutaneously introducing a guide wire into the stomach, 2) using an endoscopic to snare the guide wire and retract it through the mouth, 3) advancing a graduated dilator operating channel port assembly transorally over the guide wire under tension and partially out through the skin, and 4) anchoring the assembly into place. The steps of this aspect of the procedure will be more fully discussed later in this specification in relation to FIGS. 3a–d.

After the stomach has been insufflated through the insufflation lumens of the previously implanted ports, another needle is placed through the abdominal wall into the stomach and under endoscopic guidance a guide wire 5 is introduced and pulled out the mouth. Invagination device 70 is then passed over guide wire 5 and into esophagus 20. The introduction and advancement of invagination device 70 into esophagus 20 is facilitated by the flexibility of device 70 along its length and by the tapered shape of its distal end. Guidance of device 70 through esophagus 20 can be further facilitated by the application of appropriate tension on guide wire 5 while device 70 is being advanced. A 5 mm laparoscope 40 is introduced through the 7 mm port and invagination device 70 is positioned, under direct observation by laparoscope 40, at the anatomical gastroesophageal junction 10. The location of invagination device 70 in relation to gastroesophageal junction 10 is facilitated by the affixation of a marking 71 at a predetermined distance (3 cm) from the distal end of device 70. FIG. 1a shows invagination device 70 having been advanced into esophagus 20 and so positioned at the gastroesophageal junction 10.

The engagement assembly of invagination device 70 is then activated to advance needles 88 out through lumens 78 to project radially and forwardly from invagination device 70 and into engagement with esophagus 20. The mechanism for projecting needles 88 into engagement with esophagus 20 will be described more specifically later in this specification in relation to FIGS. 2a–b. FIG. 1b shows invagination device 70 with its engagement assembly having been so activated to extend needles 88 into engagement with esophagus 20 in the vicinity of the gastroesophageal junction. It is to be noted that FIG. 1b conceptually shows this engagement and is not drawn to scale. In practice, the engagement of needles 88 with esophagus 20 should be made as close to esophageal junction 10 as practicable. Most preferably, engagement should be made directly at the gastroesophageal junction 10 in order to prevent long term exposure of the esophogeal inner lining to the stomach secretions.

Figures 1C, 1D:
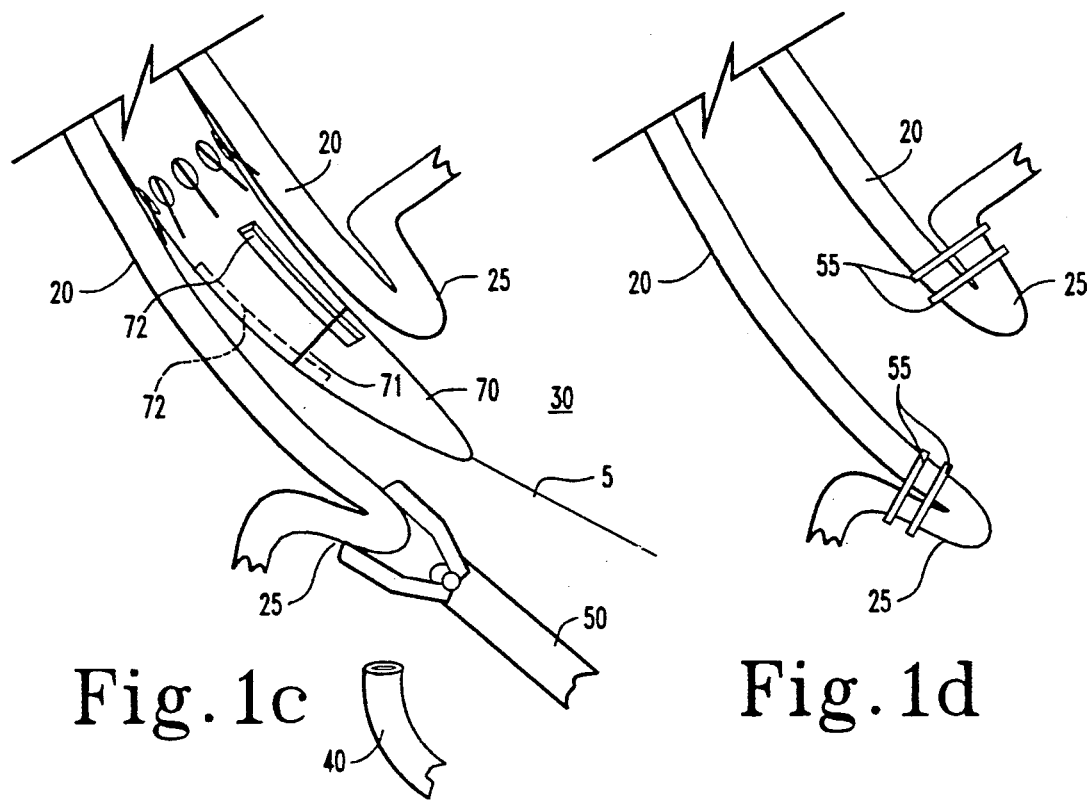

Once so engaged, invagination device 70 is pushed forward toward stomach 30, which movement forces esophagus 20 toward stomach 30 to invaginate the gastroesophageal junction 10 and involute the surrounding fundic wall 25. A 10 mm remotely operable stapling device 50 is then advanced through the previously opened 12 mm operating channel/insufflation port, and operated to staple fundic wall 25 to the invaginated gastroesophageal junction 10. Grooves 72 at the tapered distal portion of introducer guide 75 serve to facilitate the stapling action of stapler 50 by providing a stable backing therefor. FIG. 1c shows engaged invagination device 70 having been advanced toward stomach 30 to so invaginate gastroesophageal junction 10, and FIG. 1c further illustrates fundic wall 25 being fastened to the invaginated gastroesophageal junction 10 by stapler 50.

Lastly, stapler 50 is removed, needles 88 are retracted back into their respective lumens 78, and invagination device 70 and guide wire 5 are removed. Laparoscope 40 is also removed. Operating channel/insufflation ports then sealed and are kept in place for a period of time to maintain fixation of the newly formed valve. FIG. 1d shows the newly formed valve between esophagus 20 and stomach 30, with invagination device 70 and other instrumentation having been removed, and with staples 55 holding fundic wall 25 to the gastroesophageal junction 10. It is believed that two or three rows of staples 55 should be sufficient to hold the formed fold in place and maintain the functionality of the so formed valve.

Figure 2A:
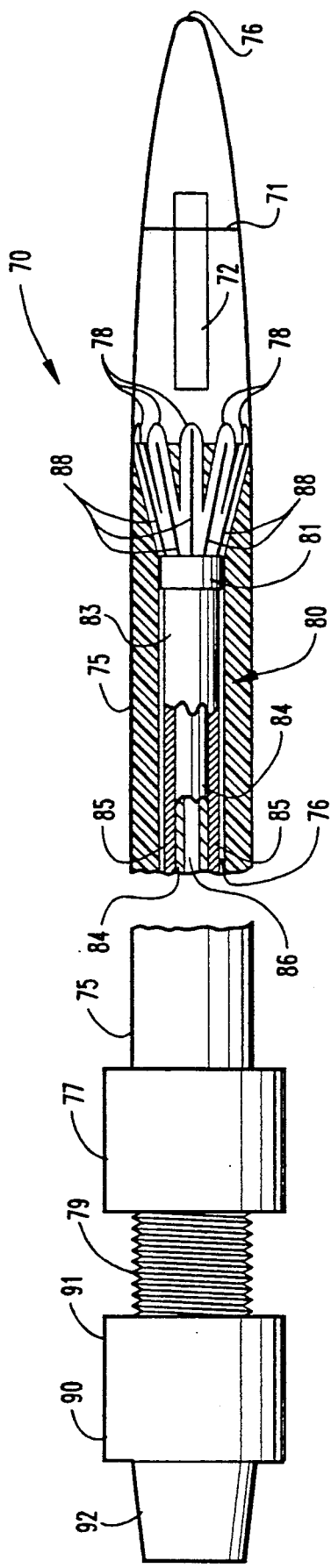
FIGS. 2a–b show partially fragmented and segmented side elevational views of the invagination device used in the described method.
Figure 2B:
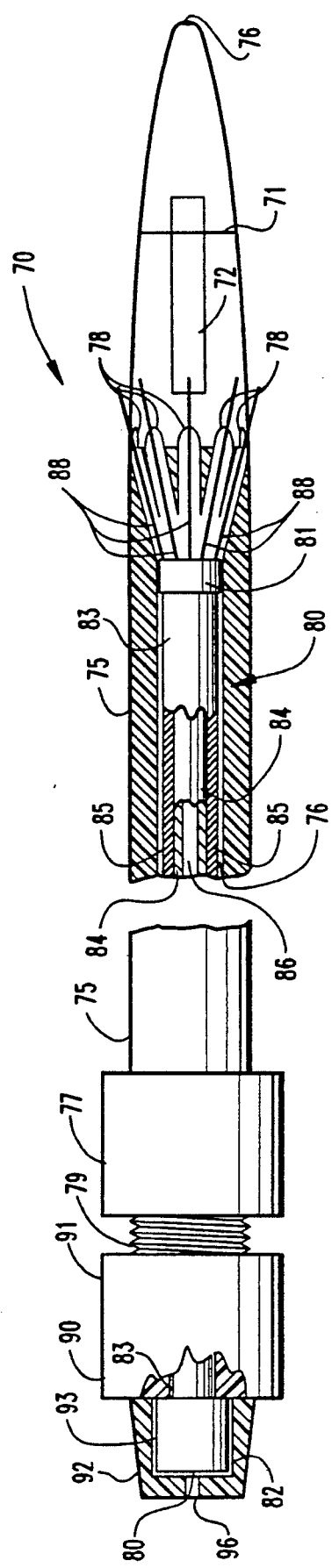

Invagination device 70 will now be discussed in specific detail in relation to FIGS. 2a–b, which show partially fragmented and segmented side elevational views of this device which is used in the above described method. FIG. 2a shows the device with its engagement assembly deactivated, the engagement needles being retained within their respective lumens. FIG. 2b shows the device with its engagement assembly activated to project the needles from their respective lumens for engagement with the esophageal wall.

Invagination device 70 includes introducer guide 75 which has an outside diameter approximating that of the esophagus. Introducer guide 75 is made with material that is biocompatible and flexible (low density polyethylene is particularly suited for this purpose), and is tapered at its distal end to facilitate insertion and advancement into the esophagus. Introducer guide 75 defines a central lumen 76, extending the length thereof, through which a guide wire is receivable. The central lumen 76 of introducer guide 75 also accommodates needle projector 80. Extending from central lumen 76 in introducer guide 75 are ten needle-receiving lumens 78, which are equidistantly spaced about the circumference of introducer guide 75 and extend to the outer diametric surface thereof. At the proximal end of introducer guide 75 is a male threaded connector 77.

Invagination device includes an engagement assembly which can be activated to project needles 88 out of their respective needle-receiving lumens 78 and into engagement with the esophagus. This engagement assembly for projecting needles 88 includes needle projector 80, advancing member 90, and connector 77.

Needle projector 80 has a metal hub 81 at its distal end to which needles 88 are connected. At its proximal end, needle projector 80 has a second metal hub 82 which is seated within recess 93 of advancing member 90. Extending along its length, the shaft 83 of needle projector 80 has a metallic interior core 84 and a plastic outer tubing 85. Metallic interior core 84 defines a central lumen 86 therein through which a guide wire is receivable. Metallic interior core 84 is made of stainless steel and provides axial strength and rigidity to shaft 83, while plastic outer tubing 85, which is constructed from low to medium density polyethylene, enhances the flexibility of shaft 83 and provides for laterally stability within the central lumen 76 of introducer guide 75. Together, hubs 81 and 82 and shaft 83 form a "push rod" which, when advanced within central lumen 76 of guide 75, projects needles 88 out of their respective needle-receiving lumens 78 and into engagement with the esophagus.

The advancement of projector 80 within central lumen 76 is accomplished by the operation of advancing member 90. Advancing member 90 has, at its distal end, a female threaded portion 91 which threadedly engages the male threaded portion 79 of connector 77 and, at its proximal end, retaining portion 92 which retains hub 82 within recess 93. Central lumen 96 through advancing member 90 receives shaft 83 and proximal hub 82 of needle projector 80, and continues through the proximal end of advancing member 90 to allow a guide wire to be passed through the entire length of invagination device 70.

By threading advancing member 90 over connector 77 of introducer guide 75, needle projector 80 is advanced within introducer guide 75 to project needles 88 out through needle-receiving lumens 78, extending needles 88 radially and forwardly about the circumference of device 70 for engagement with the esophagus. When advancing member 90 is fully threadedly engaged over connector 77, needles 88 are fully extended from introducer guide 75. By the use of the threaded engagement for advancement, needles 88 are projected smoothly and evenly to provide for a steady and sure engagement with the esophageal wall. Needles 88 are guided by needle-receiving lumens 88 out at an angle of about 30° to the longitudinal axis of device 70. Ten needles, equidistantly spaced about the circumference of device 70, 36° apart, at this projection angle of 30°, have been found to be sufficient to stably engage and advance the esophageal wall.

An operating channel/insufflation port assembly useful for the introduction of laparoscope 40 and remotely operable stapling assembly 50 will now be discussed in specific detail in relation to FIGS. 3a–d. Operating channel/insufflation port assembly 100 includes guide wire 105, operating channel/insufflation port 110, skin flange 120, attachable balloon inflator nozzle 130, attachable insufflation valve 140, sealing member 150, and seal cap 160.

Procedurally, guide wire 105 is first percutaneously introduced into the stomach, and an endoscope is introduced transorally into the stomach and used to snare guide wire 105 and retract it through the mouth. Operating channel/insufflation port 110 is then transorally advanced over guide wire 105 under tension and partially out through the skin. After removing guide wire 105, skin flange 120 is placed over the tubular portion of port 110 and advanced toward the skin. Attachable balloon inflator nozzle 130 is then attached to inflation port 112 and $CO_2$ is injected therethrough and into balloon 118, through inflation lumen 113 which is connected thereto, thus inflating balloon 118 in place within the stomach. Skin flange 120 is then adjusted against the skin to secure port 110 into place. The tapered distal portion 111 of operating channel/insufflation port 110 is then cut off at mark 111', thereby opening access into the stomach through operating channel 114.

When connected to insufflation port 115, insufflation valve 140 is operated to provide a supply of $CO_2$ into the stomach through insufflation lumen 116 and out insufflation opening 117. By turning cock 142, the supply of $CO_2$ into the stomach may be variably controlled and adjusted as needed.

Operating channel/insufflation port 110 is preferably made of flexible material which matches the elasticity of the tissue surrounding it when implanted. Silicone is believed to be particularly suited for this purpose. To provide additional strength and stability during implantation, tapered portion 111 of port 110 has a lumen 104 of only enough size to receive wire guide 105. As previously discussed, tapered portion 111 is severed after implantation to expose central operating channel 114, thereby providing access into the stomach for remotely operable instrumentation which is to be used in conjunction with the operation to be performed.

Skin flange 120 is also made of silicone, and includes of a disc shaped flange 121 and a tubular handle portion 122. Slot 123 facilitates the advancing of flange 120 along port 110. Seal cap 150 seals the end of port 110, attaching thereabout to form a sealing fit between detent 151 of seal cap 150 and indentation 119 of port 110.

Figure 3A:
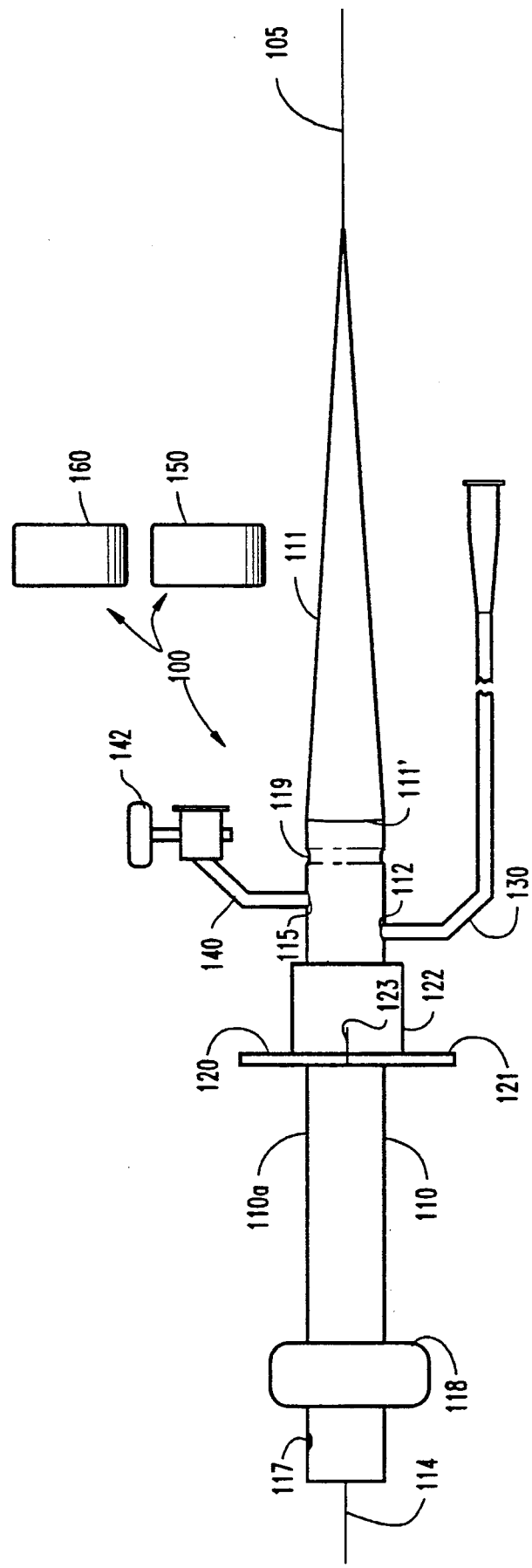
Figure 3C:
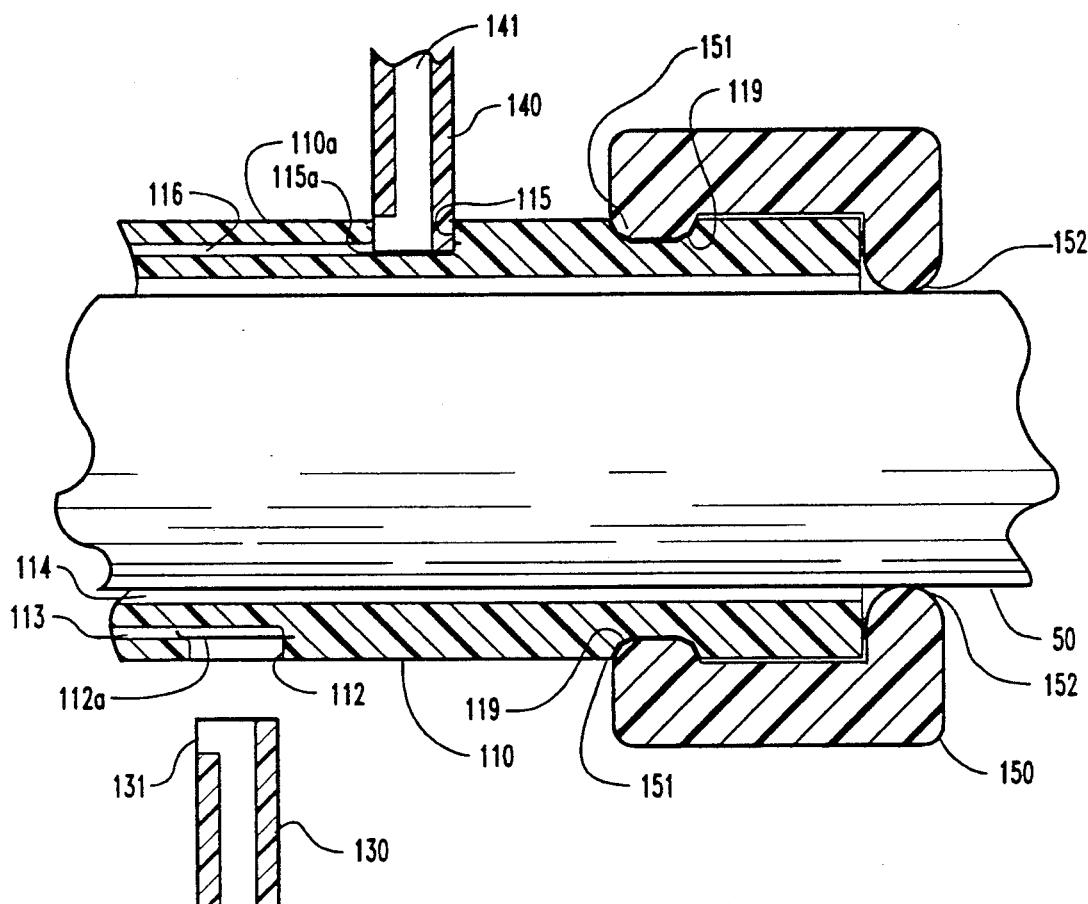
Figure 3D:
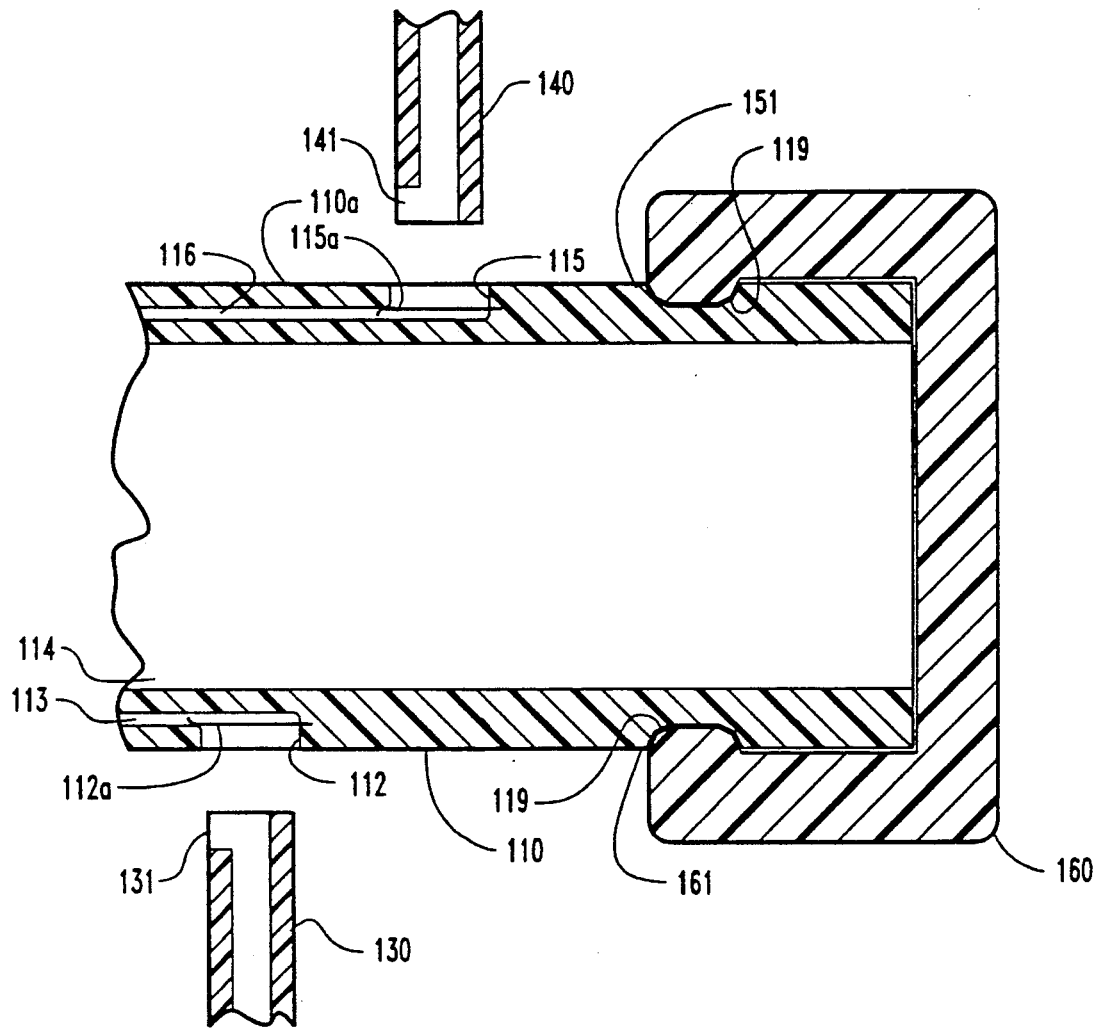

FIGS. 3b–d illustrate enlarged cross-sectional views of portions of the assembly at various stages of operation. FIG. 3b shows an implanted operating channel/insufflation port 110, balloon inflation nozzle 130, and insufflation valve 140, with nozzle 130 and valve 140 detached from their respective connection ports. In FIG. 3b it can be seen that tapered portion 111 has a central lumen 104 sized only to receive guide wire 105, thus providing additional strength and stability during implantation, while tubular portion 110a defines an enlarged operating channel 114, sized to receive remotely operable instrumentation (12 mm, for example, for a fastening assembly, and 7 mm, for a laparoscope). Within the walls of said tubular portion 110a are defined a balloon inflation port 112 and balloon inflation lumen 113 which connects port 112 to the interior of balloon 118. At the entrance of port 112 is seal 112a. Also defined within the walls of tubular portion 110a is an insufflation lumen 116, connecting exterior insufflation port 115 to interior insufflation port 117. At the entrance of port 115 is seal 115a.

Also shown in FIGS. 3b–d are partial cross-sectional views of balloon inflation nozzle 130 and insufflation valve 140, which are connectable to ports 112 and 115 respectively. When placed into port 115, as shown in FIG. 3c, seal 115a is opened, allowing $CO_2$ to be injected into the stomach through valve passageway 141 and insufflation lumen 116. When valve 140 has been removed from port 115, as shown in FIG. 3d, seal 115a recloses. Balloon inflation nozzle 130 operates in the same manner in relation to port 112 to inflate balloon 118 through passageway 131 and inflation lumen 113.

In FIG. 3c, tapered portion 111 of port 110 has been severed, and fastening assembly 50 has been inserted through central operating channel 114. Also in FIG. 3c, insufflation valve 140 has been attached to insufflation port 115 for insufflation of the stomach through insufflation lumen 116. Sealing member 150 has been placed about port 110 and positioned in sealing engagement with fastening assembly 50, thus preventing gas leakage through operating channel 114 during operation/insufflation. Detent 151 of sealing member 150 fits in indentation 119 of port 110 in sealing engagement, while interior flange 152 forms a sealing engagement with fastening assembly 50 to effectly prevent leakage.

In FIG. 3d, fastening assembly 50 has been removed, insufflation valve 140 has been detached, and seal cap 160 has been placed about port 110, sealing access to and from the stomach. So sealed, port 110 may be kept implanted for a period of time after completion of the above described operation in order to maintain fixation of the stomach to the peritoneum and also provides a drainage port for the stomach.

In the same manner as FIGS. 1a–d, FIGS. 4a–d illustrate sequential stages in the performance of an invagination technique according to the present invention in conjunction with an alternatively configured invagination device. Except as otherwise noted, all aspects of FIGS. 4a–d are the same as FIGS. 1a–d, with the primed notations of FIGS. 4a–d corresponding the same relative unprimed notations of FIGS. 1a–d. Therefore, to avoid redundancy the description of these additional drawings will not be repeated except to the extent of the following differences.

Figures 4A, 4B:
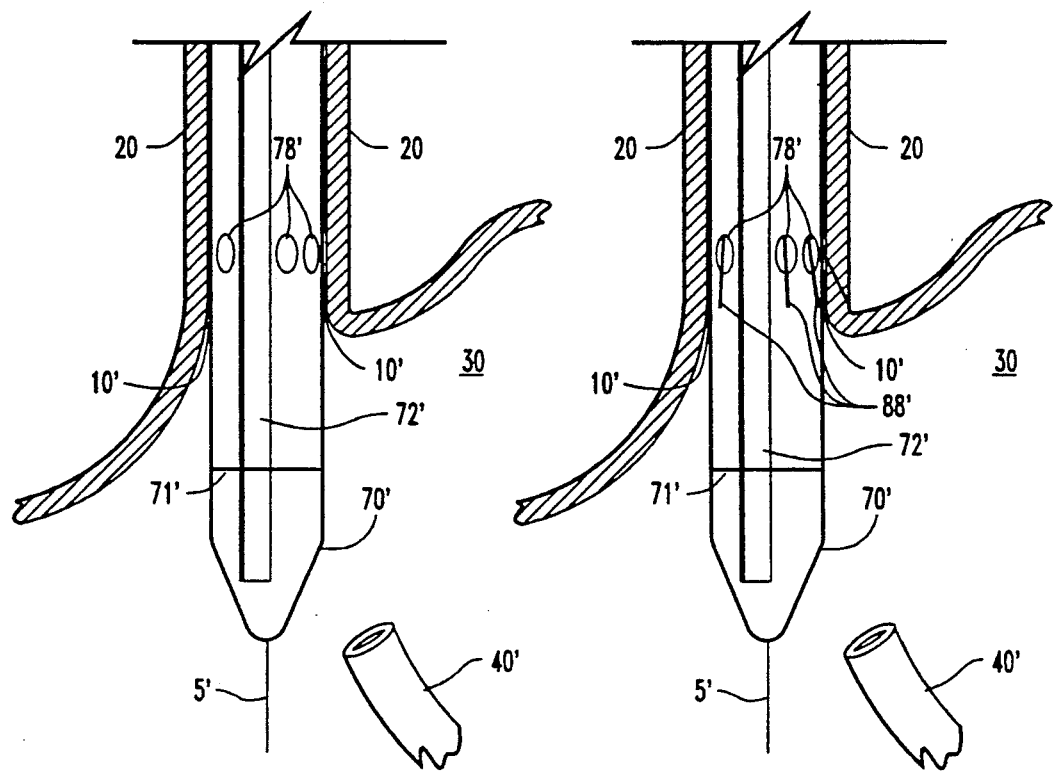
FIG. 4a shows the invagination device advanced into the esophagus and positioned at the gastroesophageal junction.
FIG. 4b shows the invagination device of FIG. 4a with its engagement assembly having been activated to extend a plurality of needles into engagement with the esophagus at the esophageal junction.
Figures 4C, 4D:
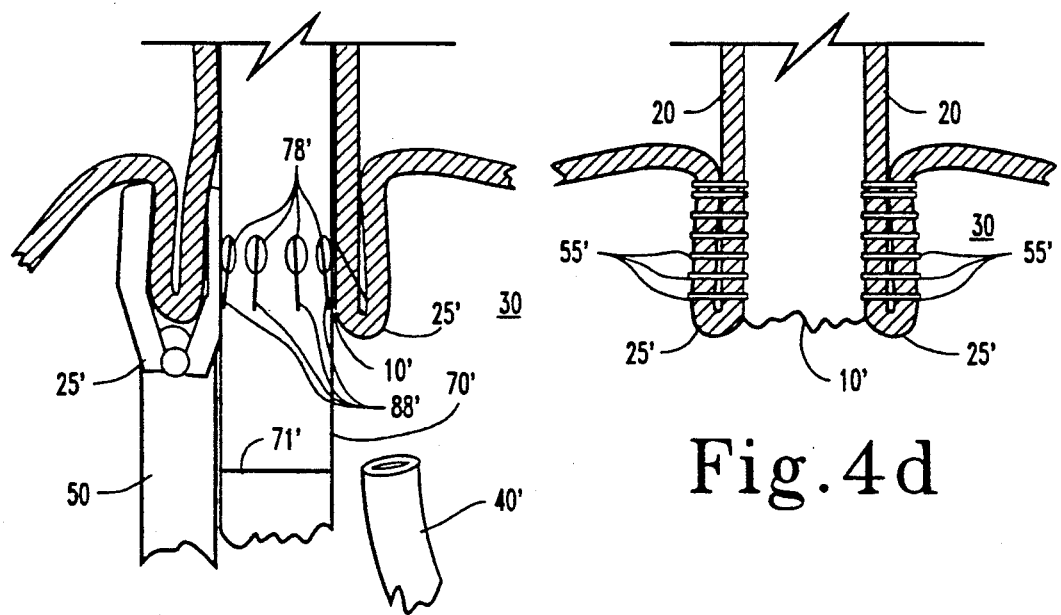
FIG. 4c shows the engaged invagination device having been advanced toward the stomach to invaginate the esophageal wall at the gastroesophageal junction, and further illustrate the invaginated gastroesophageal junction being fastened into place. Lastly.
FIG. 4d shows the newly formed valve between the esophagus and the stomach, with the invagination device and other equipment having been removed.

Specifically, in FIGS. 4a–b it is to be noted that groove 72' extends longitudinally from the beginning of the taper in guide 70' proximally past lumens 78' and that lumens 78' have been reconfigured to provide room for groove 72' to extend therepast. This revised configuration facilitates placement of the anvil jaw of fastening assembly 50' within the esophgeal lumen and allows fastening assembly 50' to be positioned past needles 88' during stapling, as shown in FIG. 4c, thus allowing the needle engagement to be made directly at the gastroesophageal junction 10. Engagement directly at the gastroesophageal junction 10 prevents long term exposure of the esophogeal inner lining to the stomach secretions.

Figure 5B:
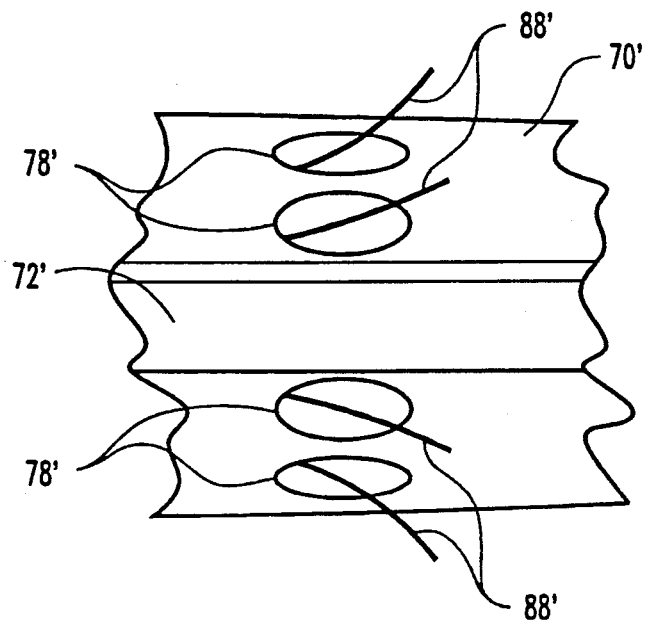
FIGS. 5a–b are enlarged illustrations, showing the changes in configuration with respect to the invagination device 70' used in relation to FIGS. 4a–d.
Figure 5A:
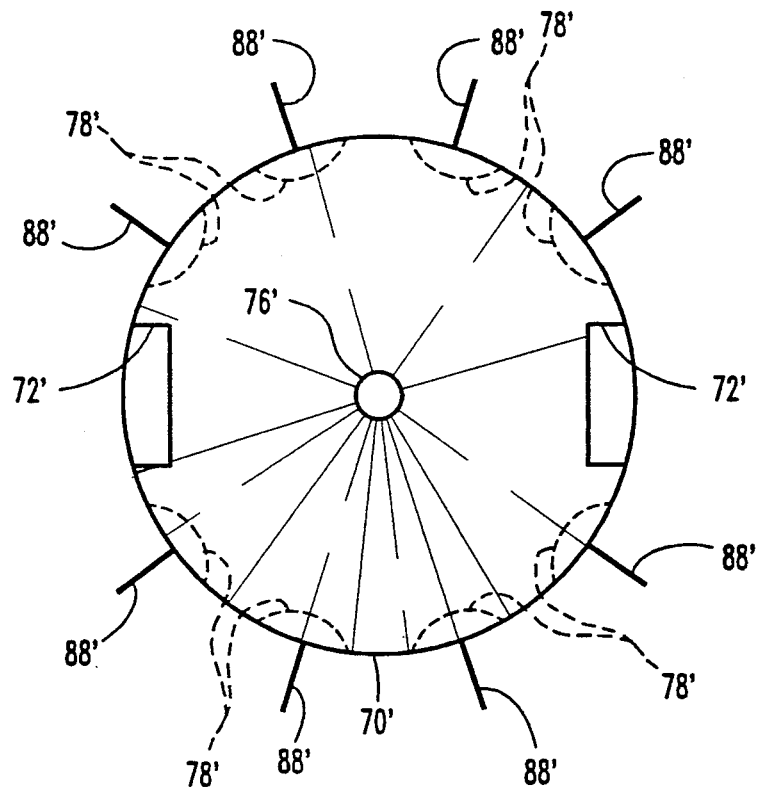

FIG. 5a shows an enlarged end view of invagination guide 70', illustrating the circumferential spacing of lumens 78' and grooves 72'. FIG. 5b is an enlarged fragmented side elevational view of invagination guide 70' showing groove 72' extending past lumens 78'.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. A method for invaginating the gastroesophageal junction of a patient, said method comprising the steps of:

introducing an invagination device transorally into the esophagus, the invagination device including an introducer guide and an engagement assembly; the introducer guide having an outside diameter approximating that of the esophagus; the engagement assembly including a plurality of needles, the needles having a retracted position in which the needles lie within the introducer guide, and an extended position in which the needles extend out of the introducer guide, projecting radially therefrom, the engagement assembly further including means for projecting the needles out of the introducer guide and into engagement with the esophagus in the vicinity of the gastroesophageal junction;

activating the engagement assembly to place the needles in their extended position in engagement with the esophagus in the vicinity of the gastroesophageal junction;

advancing the engaged invagination device toward the stomach to invaginate the gastroesophageal junction into the stomach, involuting the surrounding fundic wall;

introducing a remotely operable fastening assembly into the stomach and operating the fastening assembly to secure the invaginated gastroesophageal junction to the surrounding involuted fundic wall;

deactivating the engagement assembly to retract the extended needles from engagement and back into the needle-receiving lumens of the introducer guide; and removing the invagination device and the fastening assembly from the body of the patient.

2. The method of claim 1 additionally including the step of introducing a guide wire into the esophagus, said guide wire extending out the mouth and into the stomach, and wherein said step of introducing an invagination device includes the step of passing the invagination device over the guide wire through a central lumen defined by the invagination device.

3. The method of claim 2 additionally including the steps of extending the guide wire through the esophagus and both out the mouth and percutaneously out of the stomach, and applying tension to the so extended guide wire, and where said step of passing the invagination device over the guide wire is conducted while said tension is being applied to the guide wire.

4. The method of claim 1 wherein the needles, when extended out of the introducer guide, project radially and forwardly from the guide for engagement with the gastroesophageal junction.

5. The method of claim 1 additionally including the step of endoscopically observing the invagination device within the esophagus.

6. The method of claim 5 wherein the invaginator device is optically marked at a predetermined position in relation to its distal end.

7. A method for invaginating the gastroesophageal junction of a patient, said method comprising the steps of:

introducing an invagination device transorally into the esophagus, the invagination device including an introducer guide and an engagement assembly; the introducer guide having an outside diameter approximating that of the esophagus, the introducer guide further having a plurality of needle-receiving lumens extending to the outer diametric surface of the guide; the engagement assembly including a plurality of needles, the needles having a retracted position in which the needles lie within the needle-receiving lumens, and an extended position in which the needles extend out of the lumens and project radially from the guide, the engagement assembly further including means for projecting the needles out of the lumens and into engagement with the esophagus in the vicinity of the gastroesophageal junction;

activating the engagement assembly to place the needles in their extended position in engagement with the esophagus in the vicinity of the gastroesophageal junction;

advancing the engaged invagination device toward the stomach to invaginate the gastroesophageal junction into the stomach, involuting the surrounding fundic wall;

introducing a remotely operable fastening assembly into the stomach and operating the fastening assembly to secure the invaginated gastroesophageal junction to the surrounding involuted fundic wall;

deactivating the engagement assembly to retract the needles from engagement and back into the needle-receiving lumens of the introducer guide; and removing the invagination device and the fastening assembly from the body of the patient.

8. The method of claim 7 additionally including the step of introducing a guide wire into the esophagus, said guide wire extending out the mouth and into the stomach, and wherein said step of introducing an invagination device includes the step of passing the invagination device over the guide wire through a central lumen defined by the invagination device.

9. The method of claim 8 additionally including the steps of extending the guide wire through the esophagus and both out the mouth and percutaneously out of the stomach, and applying tension to the so extended guide wire, and where said step of passing the invagination device over the guide wire is conducted while said tension is being applied to the guide wire.

10. The method of claim 8 wherein the needles, when extended out of their respective lumens, project radially and forwardly from the guide for engagement with the esophagus.

11. The method of claim 7 additionally including the step of endoscopically observing the invagination device within the esophagus.

12. The method of claim 11 wherein the invagination device is optically marked at a predetermined position in relation to its distal end.

13. A method for invaginating the gastroesophageal junction of a patient, said method comprising the steps of:

opening at least one operating channel port into the stomach, said port being of sufficient size to accommodate a remotely operable fastening assembly;

introducing an invagination device transorally into the esophagus, the invagination device including an introducer guide and an engagement assembly; the introducer guide having an outside diameter approximating that of the esophagus, the introducer guide further having a plurality of needle-receiving lumens extending to the outer diametric surface of the guide; the engagement assembly including a plurality of needles, the needles having a retracted position in which the needles lie within the needle-receiving lumens, and an extended position in which the needles extend out of the lumens and project radially from the guide, the engagement assembly further including means for projecting the needles out of the lumens and into engagement with the gastroesophageal junction;

activating the engagement assembly to place the needles in their extended position in engagement with the gastroesophageal junction;

advancing the engaged invagination device toward the stomach to invaginate the gastroesophageal junction into the stomach, involuting the surrounding fundic wall;

introducing a remotely operable fastening assembly through the opened operating channel port into the stomach and operating the fastening assembly to secure the invaginated gastroesophageal junction to the surrounding involuted fundic wall;

deactivating the engagement assembly to retract the needles from the gastroesophageal junction and back into the needle-receiving lumens of the introducer guide; and removing the invagination device and the fastening assembly from the body of the patient, and closing said operating channel port.

14. A device for invaginating the gastroesophageal junction of a patient, said device comprising:

an introducer guide, said introducer guide having an outside diameter approximating that of the esophagus;

engagement means for engaging the gastroesophageal junction of a patient, said engagement means including a plurality of needles, said needles having a retracted position in which said needles lie within said introducer guide, and an extended position in which said needles extend out of said introducer guide and projecting radially from said guide, said engagement means further including means for projecting said needles out of said introducer guide and into engagement with the esophagus in the vicinity of the gastroesophageal junction.

15. The invagination device of claim 14 wherein said introducer guide includes means for facilitating insertion into the esophagus.

16. The invagination device of claim 15 wherein said facilitation means includes said guide being flexible along its length and tapered at its distal end.

17. The invagination device of claim 14 wherein said needles, when in their extended position, project radially and forwardly from said guide for engagement with the gastroesophageal junction.

18. The invagination device of claim 15 wherein said needles, when in their extended position, project radially and forwardly from said guide at an angle of approximately 30° in relation to the central axis of said introducer guide.

19. The invagination device of claim 18 wherein said needles are equidistantly spaced about the circumference of said introducer guide.

20. The invagination device of claim 19 wherein said engagement assembly includes 10 needles equidistantly spaced about the circumference of said introducer guide.

21. The invagination device of claim 14 wherein said introducer guide includes means for facilitating the identification of the relative positioning of said invagination device within the esophagus, said position identifying means including an optical marking positioned at a predetermined position on the exterior of said guide.

22. A device for invaginating the gastroesophageal junction of a patient, said device comprising:
an introducer guide, said introducer guide having an outside diameter approximating that of the esophagus, said guide further having a plurality of needle-receiving lumens extending to the outer diametric surface of said guide;
engagement means for engaging the gastroesophageal junction of a patient, said engagement means including a plurality of needles, said needles having a retracted position in which said needles lie within the needle-receiving lumens of said introducer guide, and an extended position in which said needles extend out of the lumens and project radially from said guide, said engagement means further including means for projecting said needles out of the needle-receiving lumens and into engagement with the esophagus in the vicinity of the gastroesophageal junction.

23. The invagination device of claim 22 wherein said guide further has a central lumen along its central axis, said plurality of needle-receiving lumens extending from said central lumen to the outer diametric surface of said guide; and wherein said engagement assembly includes a push rod, said push rod being received by said central lumen and connected to said plurality of needles, said push rod being axially movable within said central lumen of said guide to project said needles out of the needle-receiving lumens and into engagement with the gastroesophageal junction.

24. The invagination device of claim 23 wherein said push rod defines a central lumen through which a guide wire is receivable.

25. The invagination device of claim 22 wherein said introducer guide includes means for facilitating insertion into the esophagus.

26. The invagination device of claim 25 wherein said facilitation means include said guide being flexible along its length and tapered at its distal end.

27. The invagination device of claim 22 wherein said needles, when in their extended position, project radially and forwardly from said guide for engagement with the gastroesophageal junction.

28. The invagination device of claim 27 wherein said needles, when in their extended position, project radially and forwardly from said guide at an angle of approximately 30° in relation to the central axis of said introducer guide.

29. The invagination device of claim 27 wherein said needles are equidistantly spaced about the circumference of said introducer guide.

30. The invagination device of claim 28 wherein said engagement assembly includes 10 needles equidistantly spaced about the circumference of said introducer guide.

31. The invagination device of claim 23 wherein said push rod is threadedly engagable with said introducer guide and where said threaded engagement advances said push rod within said central lumen of said guide to project said needles out of the needle-receiving lumens and into engagement with the gastroesophageal junction.

32. The invagination device of claim 22 wherein said introducer guide includes means for facilitating the identification of the relative positioning of said invagination device within the esophagus, said position identifying means including an optical marking positioned at a predetermined position on the exterior of said guide.

33. The invagination device of claim 23 wherein said push rod includes an interior metal core and an outer plastic tubing.

34. The invagination device of claim 26 wherein said introducer guide is made of low density polyethylene.

35. A method for invaginating the gastroesophageal junction of a patient, said method comprising the steps of:
implanting at least one operating channel/insufflation port, the operating channel/insufflation port providing percutaneous access into the stomach for a remotely operable fastening assembly through an operating channel, and further providing a second access into the stomach for insufflating the stomach through an insufflation lumen;
insufflating the stomach through the insufflation lumen of the implanted operating channel/insufflation port;
introducing an invagination device transorally into the esophagus, the invagination device including an introducer guide and an engagement assembly; the introducer guide having an outside diameter approximating that of the esophagus; the engagement assembly including means for retractably engaging the esophagus in the vicinity of the gastroesophageal junction;
activating the engagement assembly to engage the esophagus in the vicinity of the gastroesophageal junction;
advancing the engaged invagination device toward the stomach to invaginate the gastroesophageal junction into the stomach, involuting the surrounding fundic wall;
introducing a remotely operable fastening assembly through the operating channel of the implanted operating channel/insufflation port into the stomach and operating the fastening assembly to secure the invaginated gastroesophageal junction to the surrounding involuted fundic wall;
retracting the engagement assembly from engagement with the gastroesophageal junction; and
removing the invagination device and the fastening assembly from the body of the patient.

36. The method of claim 35 additionally including the steps of:
implanting a second operating port into the stomach, said second port providing percutaneous access into the stomach for an endoscope through an operating channel; and introducing an endoscope through the operating channel of said second implanted operating channel/insufflation port into the stomach and the invagination device and the fastening assembly at the gastroesophageal junction through the so introduced endoscope.

37. The method of claim 36 in which said second port further provides a second access into the stomach for insufflating the stomach through an insufflation lumen, and further including the step of insufflating the stomach through said insufflation lumen of said second port.

38. The method of claim 35 additionally including the step of maintaining fixation of the invaginated and secured gastroesophageal junction by the leaving of said implanted port in place for a time after said removing of the invagination device and fastening assembly.

39. An operating channel/insufflation port assembly comprising:

an operating channel/insufflation port member, said operating channel/insufflation port member defining an operating channel sized to receive remotely operable instrumentation, said port member further defining an insufflation lumen connecting to an insufflation port located on the exterior of said port member;

anchoring means for anchoring said port member in place extending percutaneously into the stomach, with remotely operable instrumentation being advanceable through said operating channel and into the stomach, and with $CO_2$ being passable into the stomach through said insufflation lumen;

an insufflation valve member, connectable to said insufflation port, said insufflation valve member including means for variably controlling the supply of $CO_2$ into the stomach through said insufflation lumen; and operating channel sealing means for preventing gas leakage during operation/insufflation, said sealing means including means for providing a seal between said operating channel/insufflation port member and remotely operable instrumentation received therethrough.

* * * * *

UNITED STATES PATENT AND TRADEMARK OFFICE
CERTIFICATE OF CORRECTION

PATENT NO. : 5,088,979
DATED : February 18, 1992
INVENTOR(S) : Charles J. Filipi et al It is certified that error appears in the above-indentified patent and that said Letters Patent is hereby corrected as shown below:

In the Abstract, line 18, please delete "the", second occurrence.
In column 2, line 49, please change "cross-sectionals view" to --cross-sectional views--.
In column 4, line 56, please insert --are-- after "ports".
In column 5, line 42, please change "laterally" to --lateral--.
In column 6, line 57, please delete "of".
In column 7, line 53, please insert --to-- after "corresponding".
In column 13, line 5, please insert --observing-- after "and".

Signed and Sealed this

Fourteenth Day of September, 1993

Attest:

BRUCE LEHMAN

*Attesting Officer*       *Commissioner of Patents and Trademarks*